United States Patent
Testi et al.

(10) Patent No.: US 8,815,230 B2
(45) Date of Patent: Aug. 26, 2014

(54) METHODS FOR TREATING FRIEDREICH'S ATAXIA WITH INTERFERON GAMMA

(76) Inventors: Roberto Testi, Rome (IT); Barbara Tomassini, Rome (IT)

( * ) Notice: Subject to any disclaimer, the term of this patent is extended or adjusted under 35 U.S.C. 154(b) by 0 days.

(21) Appl. No.: 13/820,092

(22) PCT Filed: Aug. 30, 2011

(86) PCT No.: PCT/IB2011/002710
§ 371 (c)(1),
(2), (4) Date: Feb. 28, 2013

(87) PCT Pub. No.: WO2012/028961
PCT Pub. Date: Mar. 8, 2012

(65) Prior Publication Data
US 2013/0156734 A1     Jun. 20, 2013

Related U.S. Application Data

(60) Provisional application No. 61/378,284, filed on Aug. 30, 2010.

(51) Int. Cl.
*A61K 38/21*     (2006.01)
*A61K 38/00*     (2006.01)
*C07K 14/57*     (2006.01)

(52) U.S. Cl.
USPC ................... 424/85.5; 530/351; 514/1.1

(58) Field of Classification Search
None
See application file for complete search history.

(56) References Cited

U.S. PATENT DOCUMENTS

2007/0197649 A1    8/2007   Munnich et al.

FOREIGN PATENT DOCUMENTS

EP      1 378 753 A1     1/2002

OTHER PUBLICATIONS

Patent Cooperation Treaty, International Search Report and Written Opinion, International Patent Application PCT/IB2011/002710, May 3, 2012, 12 Pages.

*Primary Examiner* — Robert Landsman
*Assistant Examiner* — Bruce D Hissong
(74) *Attorney, Agent, or Firm* — Fenwick & West LLP

(57) ABSTRACT

Described herein are compositions and methods for treating Friedreich's Ataxia (FRDA) with interferon gamma. In some aspects, methods for increasing expression of frataxin in cells and for treating Friedreich's Ataxia are provided. In some additional aspects, methods increasing aconitase activity in cells are provided.

15 Claims, 5 Drawing Sheets

METHODS FOR TREATING FRIEDREICH'S ATAXIA WITH INTERFERON GAMMA

RELATED APPLICATIONS

This application is the 35 USC §371 national stage entry of PCT/IB2011/002710 and claims priority to and the benefit of the earlier filing date of U.S. Provisional Application 61/378,284 filed on Aug. 30, 2010, which is hereby incorporated by reference in its entirety for all purposes.

FIELD

The present invention relates generally to methods of treating Friedreich's Ataxia with interferon gamma.

BACKGROUND

The Disease.

FRDA is an orphan disease that affects approximately 3:100,000 individuals in Caucasian populations. Generally within 10 to 15 years from onset it leads to loss of deambulation and complete disability, with premature death often caused by cardiac insufficiency. Symptoms usually appear late in the first decade or early in the second decade of life, and include gait instability and general clumsiness. Gait ataxia has both cerebellar and sensory features, involves truncus and limbs, and is both progressive and generally unremitting. Swaying is common and, as it becomes more severe, eventually requires constant support and wheelchair use. Dysarthria occurs early in the disease and ultimately leads to complete speech impairment. Furthermore, dysphagia is a late feature and may require artificial feeding. Loss of peripheral neurons in dorsal root ganglia is the preeminent pathological finding. Ventricular hypertrophy characterizes the cardiac picture, and may progressively lead to congestive heart failure and fatal arrhythmias. A significant minority of patients also develop diabetes mellitus via mechanisms that are not yet clearly defined.

FRDA is caused by homozygous hyperexpansion of GAA triplets within the first intron of FXN, a highly conserved five-exon gene located on the long arm of human chromosome 9, coding for the protein frataxin. Pathological GAA expansions (from ~70 to >1,000 triplets) result in "sticky" DNA structures and epigenetic changes that severely reduce transcription of the FXN gene. FRDA patients live with 10-30% residual frataxin, and the severity of the disease is usually proportional to the number of GAA triplets and the consequent degree of frataxin reduction. A minority of FRDA patients, so-called compound heterozygotes, has pathological GAA expansions on one FXN allele and loss-of-function mutations on the other.

Current Therapeutic Approaches.

There is currently no specific therapy to prevent the progression of the disease. Most therapeutic approaches are aimed at reducing mitochondrial dysfunction and iron overload, and are therefore based on the use of anti-oxidants or iron chelators. While numerous approaches to treating FRDA have been explored, each of those approaches has significant limitations. Thus, a need exists in the art for new methods for more effectively treating FRDA.

SUMMARY OF THE INVENTION

The present invention provides methods for increasing expression of frataxin in cells and for treating Friedreich's Ataxia.

Provided herein is a method of increasing expression of frataxin in a cell identified as having a deficient amount of frataxin or as having Friedreich's Ataxia, comprising administering an effective amount of interferon gamma to the cell. Also provided herein is a method of increasing aconitase activity in a cell identified as having a deficient amount of aconitase activity or as having Friedreich's Ataxia, comprising administering an effective amount of interferon gamma to the cell.

In one embodiment of the invention, a method is provided for treating Friedreich's Ataxia, comprising administering to a subject diagnosed as having Friedreich's Ataxia a therapeutically effective amount of interferon gamma. In another embodiment of the invention, a method is provided for upregulating frataxin, comprising administering to a subject in need thereof a therapeutically effective amount of interferon gamma.

In one embodiment the interferon gamma has a sequence comprising or consisting of any one of the sequences in Table 2.

In still another embodiment, the interferon gamma is a recombinant form of interferon gamma. In a further embodiment, the recombinant interferon gamma is ACTIMMUNE™ or IMUKIN™. In a further embodiment, the recombinant interferon gamma comprises or consists of SEQ ID NO:2.

Provided herein is an interferon gamma for use in the treatment of Friedreich's Ataxia.

In one embodiment, the interferon gamma is recombinant.

In one embodiment, the interferon gamma consists of or comprises any one of the sequences in Table 2.

In one embodiment, the interferon gamma consists of or comprises SEQ ID NO:2.

In one embodiment, the interferon gamma ACTIMMUNE™ or IMMUKIN™.

DETAILED DESCRIPTION OF THE INVENTION

Figure 1:
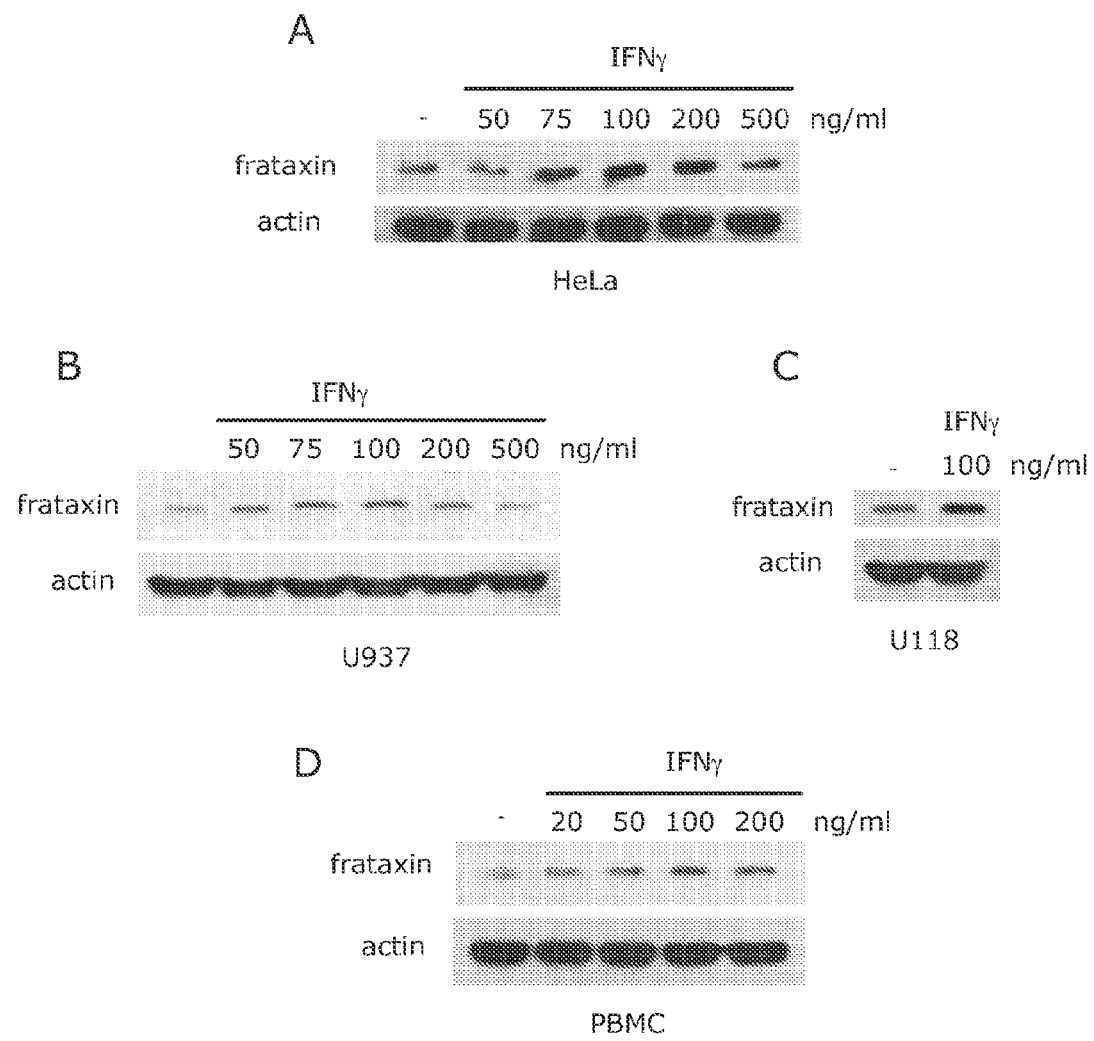
FIG. 1 Interferon gamma induces frataxin accumulation in multiple cell types.

The following explanations of terms and methods are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. For example, reference to "comprising a cell" includes one or a plurality of such cells, and so forth. The term "or" refers to a single element of stated alternative elements or a combination of two or more elements, unless the context clearly indicates otherwise.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting. Other features of the disclosure are apparent from the following detailed description and the claims.

Certain terms are discussed herein to provide additional guidance to the practitioner in describing the compositions, devices, methods and the like of aspects of the invention, and how to make or use them. It will be appreciated that the same thing can be said in more than one way. Consequently, alternative language and synonyms can be used for any one or more of the terms discussed herein. No significance is to be placed upon whether or not a term is elaborated or discussed herein. Some synonyms or substitutable methods, materials and the like are provided. Recital of one or a few synonyms or equivalents does not exclude use of other synonyms or equivalents, unless it is explicitly stated. Use of examples, including examples of terms, is for illustrative purposes only and does not limit the scope and meaning of the aspects of the invention herein.

All publications, references, issued patents and patent applications cited within the body of the specification are hereby incorporated by reference in their entirety, for all purposes.

The term "peptide" as used herein refers to a short polypeptide, e.g., one that is typically less than about 50 amino acids long and more typically less than about 30 amino acids long. The term as used herein encompasses analogs and mimetics that mimic structural and thus biological function.

The term "isolated protein" or "isolated polypeptide" is a protein or polypeptide that by virtue of its origin or source of derivation (1) is not associated with naturally associated components that accompany it in its native state, (2) exists in a purity not found in nature, where purity can be adjudged with respect to the presence of other cellular material (e.g., is free of other proteins from the same species) (3) is expressed by a cell from a different species, or (4) does not occur in nature (e.g., it is a fragment of a polypeptide found in nature or it includes amino acid analogs or derivatives not found in nature or linkages other than standard peptide bonds). Thus, a polypeptide that is chemically synthesized or synthesized in a cellular system different from the cell from which it naturally originates will be "isolated" from its naturally associated components. A polypeptide or protein may also be rendered substantially free of naturally associated components by isolation, using protein purification techniques well known in the art. As thus defined, "isolated" does not necessarily require that the protein, polypeptide, peptide or oligopeptide so described has been physically removed from its native environment.

A protein has "homology" or is "homologous" to a second protein if the nucleic acid sequence that encodes the protein has a similar sequence to the nucleic acid sequence that encodes the second protein. Alternatively, a protein has homology to a second protein if the two proteins have "similar" amino acid sequences. (Thus, the term "homologous proteins" is defined to mean that the two proteins have similar amino acid sequences.) As used herein, homology between two regions of amino acid sequence (especially with respect to predicted structural similarities) is interpreted as implying similarity in function.

When "homologous" is used in reference to proteins or peptides, it is recognized that residue positions that are not identical often differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of homology may be adjusted upwards to correct for the conservative nature of the substitution. Means for making this adjustment are well known to those of skill in the art. See, e.g., Pearson, 1994, *Methods Mol. Biol.* 24:307-31 and 25:365-89 (herein incorporated by reference).

The following six groups each contain amino acids that are conservative substitutions for one another: 1) Serine (S), Threonine (T); 2) Aspartic Acid (D), Glutamic Acid (E); 3) Asparagine (N), Glutamine (Q); 4) Arginine (R), Lysine (K); 5) Isoleucine (I), Leucine (L), Methionine (M), Alanine (A), Valine (V), and 6) Phenylalanine (F), Tyrosine (Y), Tryptophan (W). Table 1 is a general BLOSUM62 amino acid substitution matrix.

TABLE 1

BLOSUM62 amino acid substitution matrix.
Reference: Henikoff, S. and Henikoff, J. G. (1992). Amino acid substitution matrices from protein blocks. Proc. Natl. Acad. Sci. USA 89: 10915-10919.

|   | A | B | C | D | E | F | G | H | I | K | L | M | N | P | Q | R | S | T | V | W | X | Y | Z |
|---|---|---|---|---|---|---|---|---|---|---|---|---|---|---|---|---|---|---|---|---|---|---|---|
| A | 4 | -2 | 0 | -2 | -1 | -2 | 0 | -2 | -1 | -1 | -1 | -1 | -2 | -1 | -1 | -1 | 1 | 0 | 0 | -3 | -1 | -2 | -1 |
| B | -2 | 6 | -3 | 6 | 2 | -3 | -1 | -1 | -3 | -1 | -4 | -3 | 1 | -1 | 0 | -2 | 0 | -1 | -3 | -4 | -1 | -3 | 2 |
| C | 0 | -3 | 9 | -3 | -4 | -2 | -3 | -3 | -1 | -3 | -1 | -1 | -3 | -3 | -3 | -3 | -1 | -1 | -1 | -2 | -1 | -2 | -4 |
| D | -2 | 6 | -3 | 6 | 2 | -3 | -1 | -1 | -3 | -1 | -4 | -3 | 1 | -1 | 0 | -2 | 0 | -1 | -3 | -4 | -1 | -3 | 2 |
| E | -1 | 2 | -4 | 2 | 5 | -3 | -2 | 0 | -3 | 1 | -3 | -2 | 0 | -1 | 2 | 0 | 0 | -1 | -2 | -3 | -1 | -2 | 5 |
| F | -2 | -3 | -2 | -3 | -3 | 6 | -3 | -1 | 0 | -3 | 0 | 0 | -3 | -4 | -3 | -3 | -2 | -2 | -1 | 1 | -1 | 3 | -3 |
| G | 0 | -1 | -3 | -1 | -2 | -3 | 6 | -2 | -4 | -2 | -4 | -3 | 0 | -2 | -2 | -2 | 0 | -2 | -3 | -2 | -1 | -3 | -2 |
| H | -2 | -1 | -3 | -1 | 0 | -1 | -2 | 8 | -3 | -1 | -3 | -2 | 1 | -2 | 0 | 0 | -1 | -2 | -3 | -2 | -1 | 2 | 0 |
| I | -1 | -3 | -1 | -3 | -3 | 0 | -4 | -3 | 4 | -3 | 2 | 1 | -3 | -3 | -3 | -3 | -2 | -1 | 3 | -3 | -1 | -1 | -3 |
| K | -1 | -1 | -3 | -1 | 1 | -3 | -2 | -1 | -3 | 5 | -2 | -1 | 0 | -1 | 1 | 2 | 0 | -1 | -2 | -3 | -1 | -2 | 1 |
| L | -1 | -4 | -1 | -4 | -3 | 0 | -4 | -3 | 2 | -2 | 4 | 2 | -3 | -3 | -2 | -2 | -2 | -1 | 1 | -2 | -1 | -1 | -3 |
| M | -1 | -3 | -1 | -3 | -2 | 0 | -3 | -2 | 1 | -1 | 2 | 5 | -2 | -2 | 0 | -1 | -1 | -1 | 1 | -1 | -1 | -1 | -2 |
| N | -2 | 1 | -3 | 1 | 0 | -3 | 0 | 1 | -3 | 0 | -3 | -2 | 6 | -2 | 0 | 0 | 1 | 0 | -3 | -4 | -1 | -2 | 0 |
| P | -1 | -1 | -3 | -1 | -1 | -4 | -2 | -2 | -3 | -1 | -3 | -2 | -2 | 7 | -1 | -2 | -1 | -1 | -2 | -4 | -1 | -3 | -1 |
| Q | -1 | 0 | -3 | 0 | 2 | -3 | -2 | 0 | -3 | 1 | -2 | 0 | 0 | -1 | 5 | 1 | 0 | -1 | -2 | -2 | -1 | -1 | 2 |
| R | -1 | -2 | -3 | -2 | 0 | -3 | -2 | 0 | -3 | 2 | -2 | -1 | 0 | -2 | 1 | 5 | -1 | -1 | -3 | -3 | -1 | -2 | 0 |
| S | 1 | 0 | -1 | 0 | 0 | -2 | 0 | -1 | -2 | 0 | -2 | -1 | 1 | -1 | 0 | -1 | 4 | 1 | -2 | -3 | -1 | -2 | 0 |
| T | 0 | -1 | -1 | -1 | -1 | -2 | -2 | -2 | -1 | -1 | -1 | -1 | 0 | -1 | -1 | -1 | 1 | 5 | 0 | -2 | -1 | -2 | -1 |
| V | 0 | -3 | -1 | -3 | -2 | -1 | -3 | -3 | 3 | -2 | 1 | 1 | -3 | -2 | -2 | -3 | -2 | 0 | 4 | -3 | -1 | -1 | -2 |

TABLE 1-continued

BLOSUM62 amino acid substitution matrix.
Reference: Henikoff, S. and Henikoff, J. G. (1992). Amino acid substitution
matrices from protein blocks. Proc. Natl. Acad. Sci. USA 89: 10915-10919.

|   | A  | B  | C  | D  | E  | F  | G  | H  | I  | K  | L  | M  | N  | P  | Q  | R  | S  | T  | V  | W  | X  | Y  | Z  |
|---|----|----|----|----|----|----|----|----|----|----|----|----|----|----|----|----|----|----|----|----|----|----|----|
| W | -3 | -4 | -2 | -4 | -3 | 1  | -2 | -2 | -3 | -3 | -2 | -1 | -4 | -4 | -2 | -3 | -3 | -2 | -3 | 11 | -1 | 2  | -3 |
| X | -1 | -1 | -1 | -1 | -1 | -1 | -1 | -1 | -1 | -1 | -1 | -1 | -1 | -1 | -1 | -1 | -1 | -1 | -1 | -1 | -1 | -1 | -1 |
| Y | -2 | -3 | -2 | -3 | -2 | 3  | -3 | 2  | -1 | -2 | -1 | -1 | -2 | -3 | -1 | -2 | -2 | -1 | -1 | 2  | -1 | 7  | -2 |
| Z | -1 | 2  | -4 | 2  | 5  | -3 | -2 | 0  | -3 | 1  | -3 | -2 | 0  | -1 | 2  | 0  | 0  | -1 | -2 | -3 | -1 | -2 | 5  |

Sequence homology for polypeptides, which is also referred to as percent sequence identity, is typically measured using sequence analysis software. See, e.g., the Sequence Analysis Software Package of the Genetics Computer Group (GCG), University of Wisconsin Biotechnology Center, 910 University Avenue, Madison, Wis. 53705. Protein analysis software matches similar sequences using a measure of homology assigned to various substitutions, deletions and other modifications, including conservative amino acid substitutions. For instance, GCG contains programs such as "Gap" and "Bestfit" which can be used with default parameters to determine sequence homology or sequence identity between closely related polypeptides, such as homologous polypeptides from different species of organisms or between a wild-type protein and a mutein thereof. See, e.g., GCG Version 6.1.

A preferred algorithm when comparing a particular polypeptide sequence to a database containing a large number of sequences from different organisms is the computer program BLAST (Altschul et al., *J. Mol. Biol.* 215:403-410 (1990); Gish and States, *Nature Genet.* 3:266-272 (1993); Madden et al., *Meth. Enzymol.* 266:131-141 (1996); Altschul et al., *Nucleic Acids Res.* 25:3389-3402 (1997); Zhang and Madden, *Genome Res.* 7:649-656 (1997)), especially blastp or tblastn (Altschul et al., *Nucleic Acids Res.* 25:3389-3402 (1997)).

Preferred parameters for BLASTp are: Expectation value: 10 (default); Filter: seg (default); Cost to open a gap: 11 (default); Cost to extend a gap: 1 (default); Max. alignments: 100 (default); Word size: 11 (default); No. of descriptions: 100 (default); Penalty Matrix: BLOSUM62.

One skilled in the art may also use the ALIGN program incorporating the non-linear algorithm of Myers and Miller (*Comput. Appl. Biosci.* (1988) 4:11-17). For amino acid sequence comparison using the ALIGN program one skilled in the art may use a PAM120 weight residue table, a gap length penalty of 12, and a gap penalty of 4.

The length of polypeptide sequences compared for homology will generally be at least about 16 amino acid residues, usually at least about 20 residues, more usually at least about 24 residues, typically at least about 28 residues, and preferably more than about 35 residues. When searching a database containing sequences from a large number of different organisms, it is preferable to compare amino acid sequences. Database searching using amino acid sequences can be measured by algorithms other than blastp known in the art. For instance, polypeptide sequences can be compared using FASTA, a program in GCG Version 6.1. FASTA provides alignments and percent sequence identity of the regions of the best overlap between the query and search sequences. Pearson, *Methods Enzymol.* 183:63-98 (1990) (herein incorporated by reference). For example, percent sequence identity between amino acid sequences can be determined using FASTA with its default parameters (a word size of 2 and the PAM250 scoring matrix), as provided in GCG Version 6.1, herein incorporated by reference.

Nucleic Acid Molecule: The term "nucleic acid molecule" or "polynucleotide" refers to a polymeric form of nucleotides of at least 10 bases in length. The term includes DNA molecules (e.g., cDNA or genomic or synthetic DNA) and RNA molecules (e.g., mRNA or synthetic RNA), as well as analogs of DNA or RNA containing non-natural nucleotide analogs, non-native inter-nucleoside bonds, or both. The nucleic acid can be in any topological conformation. For instance, the nucleic acid can be single-stranded, double-stranded, triple-stranded, quadruplexed, partially double-stranded, branched, hair-pinned, circular, or in a padlocked conformation. If single stranded, the nucleic acid molecule can be the sense strand or the antisense strand. "Nucleic acid molecule" includes nucleic acid molecules which are not naturally occurring.

Isolated: An "isolated" nucleic acid or polynucleotide (e.g., an RNA, DNA or a mixed polymer) is one which is substantially separated from other cellular components that naturally accompany the native polynucleotide in its natural host cell, e.g., ribosomes, polymerases, and genomic sequences with which it is naturally associated. The term embraces a nucleic acid or polynucleotide that (1) has been removed from its naturally occurring environment, (2) is not associated with all or a portion of a polynucleotide in which the "isolated polynucleotide" is found in nature, (3) is operatively linked to a polynucleotide which it is not linked to in nature, or (4) does not occur in nature. The term "isolated" or "substantially pure" also can be used in reference to recombinant or cloned DNA isolates, chemically synthesized polynucleotide analogs, or polynucleotide analogs that are biologically synthesized by heterologous systems. However, "isolated" does not necessarily require that the nucleic acid or polynucleotide so described has itself been physically removed from its native environment. For instance, an endogenous nucleic acid sequence in the genome of an organism is deemed "isolated" herein if a heterologous sequence (i.e., a sequence that is not naturally adjacent to this endogenous nucleic acid sequence) is placed adjacent to the endogenous nucleic acid sequence, such that the expression of this endogenous nucleic acid sequence is altered. By way of example, a non native promoter sequence can be substituted (e.g. by homologous recombination) for the native promoter of a gene in the genome of a human cell, such that this gene has an altered expression pattern. This gene would now become "isolated" because it is separated from at least some of the sequences that naturally flank it. A nucleic acid is also considered "isolated" if it contains any modifications that do not naturally occur to the corresponding nucleic acid in a genome. For instance, an endogenous coding sequence is considered "isolated" if it contains an insertion, deletion or a point mutation introduced artificially, e.g. by human intervention. An "isolated nucleic acid" also includes a nucleic acid integrated into a host cell chromosome at a heterologous site, as well as a nucleic acid construct present as an episome. Moreover, an "isolated nucleic acid" can be substantially free of other cellular material, or substantially free of culture medium when produced by recombinant techniques, or substantially free of chemical precursors or other chemicals when chemically synthesized. The term also embraces nucleic acid molecules and proteins prepared by recombinant expression in a host cell as well as chemically synthesized nucleic acid molecules and proteins.

The term "percent sequence identity" or "identical" in the context of nucleic acid sequences refers to the residues in the two sequences which are the same when aligned for maximum correspondence. The length of sequence identity comparison may be over a stretch of at least about nine nucleotides, usually at least about 20 nucleotides, more usually at least about 24 nucleotides, typically at least about 28 nucleotides, more typically at least about 32 nucleotides, and preferably at least about 36 or more nucleotides. There are a number of different algorithms known in the art which can be used to measure nucleotide sequence identity. For instance, polynucleotide sequences can be compared using FASTA, Gap or Bestfit, which are programs in Wisconsin Package Version 10.0, Genetics Computer Group (GCG), Madison, Wis. FASTA provides alignments and percent sequence identity of the regions of the best overlap between the query and search sequences. Pearson, *Methods Enzymol.* 183:63-98 (1990) (hereby incorporated by reference in its entirety). For instance, percent sequence identity between nucleic acid sequences can be determined using FASTA with its default parameters (a word size of 6 and the NOPAM factor for the scoring matrix) or using Gap with its default parameters as provided in GCG Version 6.1, herein incorporated by reference. Alternatively, sequences can be compared using the computer program, BLAST (Altschul et al., *J. Mol. Biol.* 215:403-410 (1990); Gish and States, *Nature Genet.* 3:266-272 (1993); Madden et al., *Meth. Enzymol.* 266:131-141 (1996); Altschul et al., *Nucleic Acids Res.* 25:3389-3402 (1997); Zhang and Madden, *Genome Res.* 7:649-656 (1997)), especially blastp or tblastn (Altschul et al., *Nucleic Acids Res.* 25:3389-3402 (1997)).

A particular, non-limiting example of a mathematical algorithm utilized for the comparison of sequences is that of Karlin and Altschul (*Proc. Natl. Acad. Sci.* (1990) USA 87:2264-68; *Proc. Natl. Acad. Sci.* USA (1993) 90: 5873-77) as used in the NBLAST and XBLAST programs (version 2.0) of Altschul et al. (*J. Mol. Biol.* (1990) 215:403-10). BLAST nucleotide searches can be performed with the NBLAST program, score=100, wordlength=12 to obtain nucleotide sequences homologous to nucleic acid molecules of the invention. To obtain gapped alignments for comparison purposes, Gapped BLAST can be utilized as described in Altschul et al. (*Nucleic Acids Research* (1997) 25(17):3389-3402). When utilizing BLAST and Gapped BLAST programs, the default parameters of the respective programs (e.g., XBLAST and NBLAST) can be used (see website for BLAST hosted by the National Center for Biotechnology Information).

Purified: The term purified does not require absolute purity; rather, it is intended as a relative term. Thus, for example, a purified product preparation, is one in which the product is more concentrated than the product is in its environment within a cell. As used herein, a composition that is a "substantially pure" compound is substantially free of one or more other compounds, i.e., the composition contains greater than 80 vol. %, greater than 90 vol. %, greater than 95 vol. %, greater than 96 vol. %, greater than 97 vol. %, greater than 98 vol. %, greater than 99 vol. %, greater than 99.5 vol. %, greater than 99.6 vol. %, greater than 99.7 vol. %, greater than 99.8 vol. %, or greater than 99.9 vol. % of the compound; or less than 20 vol. %, less than 10 vol. %, less than 5 vol. %, less than 3 vol. %, less than 1 vol. %, less than 0.5 vol. %, less than 0.1 vol. %, or less than 0.01 vol. % of the one or more other compounds, based on the total volume of the composition.

Recombinant: A recombinant nucleic acid molecule or protein is one that has a sequence that is not naturally occurring, has a sequence that is made by an artificial combination of two otherwise separated segments of sequence, or both. This artificial combination can be achieved, for example, by chemical synthesis or by the artificial manipulation of isolated segments of nucleic acid molecules or proteins, such as genetic engineering techniques. Recombinant is also used to describe nucleic acid molecules that have been artificially manipulated, but contain the same regulatory sequences and coding regions that are found in the organism from which the nucleic acid was isolated.

"Specific binding" refers to the ability of two molecules to bind to each other in preference to binding to other molecules in the environment. Typically, "specific binding" discriminates over adventitious binding in a reaction by at least two-fold, more typically by at least 10-fold, often at least 100-fold. Typically, the affinity or avidity of a specific binding reaction, as quantified by a dissociation constant, is about $10^{-7}$ M or stronger (e.g., about $10^{-8}$ M, $10^{-9}$ M or even stronger).

In general, "stringent hybridization" is performed at about 25° C. below the thermal melting point ($T_m$) for the specific DNA hybrid under a particular set of conditions. "Stringent washing" is performed at temperatures about 5° C. lower than the $T_m$ for the specific DNA hybrid under a particular set of conditions. The $T_m$ is the temperature at which 50% of the target sequence hybridizes to a perfectly matched probe. See Sambrook et al., *Molecular Cloning: A Laboratory Manual*, 2d ed., Cold Spring Harbor Laboratory Press, Cold Spring Harbor, N.Y. (1989), page 9.51, hereby incorporated by reference. For purposes herein, "stringent conditions" are defined for solution phase hybridization as aqueous hybridization (i.e., free of formamide) in 6×SSC (where 20×SSC contains 3.0 M NaCl and 0.3 M sodium citrate), 1% SDS at 65° C. for 8-12 hours, followed by two washes in 0.2×SSC, 0.1% SDS at 65° C. for 20 minutes. It will be appreciated by the skilled worker that hybridization at 65° C. will occur at different rates depending on a number of factors including the length and percent identity of the sequences which are hybridizing.

A preferred, non-limiting example of stringent hybridization conditions includes hybridization in 4× sodium chloride/sodium citrate (SSC), at about 65-70° C. (or hybridization in 4×SSC plus 50% formamide at about 42-50° C.) followed by one or more washes in 1×SSC, at about 65-70° C. A preferred, non-limiting example of highly stringent hybridization conditions includes hybridization in 1×SSC, at about 65-70° C. (or hybridization in 1×SSC plus 50% formamide at about 42-50° C.) followed by one or more washes in 0.3×SSC, at about 65-70° C. A preferred, non-limiting example of reduced stringency hybridization conditions includes hybridization in 4×SSC, at about 50-60° C. (or alternatively hybridization in 6×SSC plus 50% formamide at about 40-45° C.) followed by one or more washes in 2×SSC, at about 50-60° C. Intermediate ranges e.g., at 65-70° C. or at 42-50° C. are also within the scope of the invention. SSPE (1×SSPE is 0.15 M NaCl, 10 mM $NaH_2PO_4$, and 1.25 mM EDTA, pH 7.4) can be substituted for SSC (1×SSC is 0.15 M NaCl and 15 mM sodium citrate) in the hybridization and wash buffers; washes are performed for 15 minutes each after hybridization is complete. The hybridization temperature for hybrids anticipated to be less than 50 base pairs in length should be 5-10° C. less than the melting temperature ($T_m$) of the hybrid, where $T_m$ is determined according to the following equations. For hybrids less than 18 base pairs in length, $T_m$ (° C.)=2(# of A+T bases)+4(# of G+C bases). For hybrids between 18 and 49 base pairs in length, $T_m$(° C.)=81.5+16.6($\log_{10}$ [Na$^+$])+0.41 (% G+C)−(600/N), where N is the number of bases in the hybrid, and [Na$^+$] is the concentration of sodium ions in the hybridization buffer ([Na$^+$] for 1×SSC=0.165 M).

The skilled practitioner recognizes that reagents can be added to hybridization and/or wash buffers. For example, to decrease non-specific hybridization of nucleic acid molecules to, for example, nitrocellulose or nylon membranes, blocking agents, including but not limited to, BSA or salmon or herring sperm carrier DNA and/or detergents, including but not limited to, SDS, chelating agents EDTA, Ficoll, PVP and the like can be used. When using nylon membranes, in particular, an additional, non-limiting example of stringent hybridization conditions is hybridization in 0.25-0.5M NaH$_2$PO$_4$, 7% SDS at about 65° C., followed by one or more washes at 0.02M NaH$_2$PO$_4$, 1% SDS at 65° C. (Church and Gilbert (1984) *Proc. Natl. Acad. Sci.* USA 81:1991-1995) or, alternatively, 0.2×SSC, 1% SDS.

The term "substantial homology" or "substantial similarity," when referring to a nucleic acid or fragment thereof, indicates that, when optimally aligned with appropriate nucleotide insertions or deletions with another nucleic acid (or its complementary strand), there is nucleotide sequence identity in at least about 71%, 72%, 73%, 74%, 75%, 76%, 77%, 78%, 79%, 80%, 81%, 82%, 83%, 84%, 85%, preferably at least about 90%, and more preferably at least about 95%, 96%, 97%, 98% or 99% of the nucleotide bases, as measured by any well-known algorithm of sequence identity, such as FASTA, BLAST or Gap, as discussed above.

Alternatively, substantial homology or similarity exists when a nucleic acid or fragment thereof hybridizes to another nucleic acid, to a strand of another nucleic acid, or to the complementary strand thereof, under stringent hybridization conditions. "Stringent hybridization conditions" and "stringent wash conditions" in the context of nucleic acid hybridization experiments depend upon a number of different physical parameters. Nucleic acid hybridization will be affected by such conditions as salt concentration, temperature, solvents, the base composition of the hybridizing species, length of the complementary regions, and the number of nucleotide base mismatches between the hybridizing nucleic acids, as will be readily appreciated by those skilled in the art. One having ordinary skill in the art knows how to vary these parameters to achieve a particular stringency of hybridization.

Vector: The term "vector" as used herein refers to a nucleic acid molecule capable of transporting another nucleic acid to which it has been linked. One type of vector is a "plasmid," which refers to a circular double stranded DNA loop into which additional DNA segments may be ligated. Other vectors include cosmids, bacterial artificial chromosomes (BACs) and yeast artificial chromosomes (YACs). Another type of vector is a viral vector, wherein additional DNA segments may be ligated into the viral genome (discussed in more detail below). Certain vectors are capable of autonomous replication in a host cell into which they are introduced (e.g., vectors having an origin of replication which functions in the host cell). Other vectors can be integrated into the genome of a host cell upon introduction into the host cell, and are thereby replicated along with the host genome. Moreover, certain preferred vectors are capable of directing the expression of genes to which they are operatively linked. Such vectors are referred to herein as "recombinant expression vectors" (or simply, "expression vectors"). A vector can also include one or more selectable marker genes and other genetic elements known in the art. When stable expression results from integration, the site of the construct's integration can occur randomly within the host genome or can be targeted through the use of constructs containing regions of homology with the host genome sufficient to target recombination with the host locus. Where constructs are targeted to an endogenous locus, all or some of the transcriptional and translational regulatory regions can be provided by the endogenous locus.

Modulation of Frataxin Levels by Interferon Gamma (IFNγ)

IFNγ is a cytokine that exists in a dimer. IFNγ is found in many mammals, including humans. When formed, human IFNγ has 166 amino acids SEQ ID NO: 3 (MKYTSYILAF QLCIVLGSLG CYCQDPYVKE AENLKKYFNA GHSD-VADNGT LFLGILKNWK EESDRKIMQS QIVSFYFKLF KNFKDDQSIQ KSVETIKEDM NVKFFNSNKK KRD-DFEKLTN YSVTDLNVQR KAIHELIQVM AEL-SPAAKTG KRKRSQMLFR GRRASQ). Before secretion from the cell, the first 23 amino acids, the signal peptide, are removed to generate the 143 amino acid mature IFNγ. (SEQ ID NO: 4—see Table 2). The propeptide at the end of the sequence is also removed resulting in SEQ ID NO: 5 (see Table 2).

Natural variations of IFNγ include amino acid substitutions at K29Q and R160Q with positions determined in the full 166 amino acid sequence. Human IFNγ with one or both of those variations would be as follows: SEQ ID NO: 6 (MKYTSY-ILAFQLCIVLGSLGCYCQDPYVQEAEN-LKKYFNAGHSDVADNGTLFLGILK NWKEESDRKIM-QSQIVSFYFKLFKNFKDDQSIQKSVETIKEDMNVKFF NSNKKKRDDF EKLTNYSVTDLNVQRKAIHELIQV-MAELSPAAKTGKRKRSQMLFRGRRASQ) is the full 166 amino acid sequence of K29Q IFNγ. SEQ ID NO: 7 (see Table 2) is mature K29Q IFNγ. SEQ ID NO: 8 (see Table 2) is mature K29Q IFNγ without the propeptide. SEQ ID NO: 9 (MKYTSYILAFQLCIVLGSLGCYCQD-PYVKEAENLKKYFNAGHSDVADNGTLFLGILK NWKEESDRKIMQSQIVSFYFKLFKNFKD-DQSIQKSVETIKEDMNVKFFNSNKKKRDDF EKLT-NYSVTDLNVQRKAIHELIQVMAEL-SPAAKTGKRKRSQMLFQGRRASQ) is the full 166 amino acid sequence of R160Q IFNγ. SEQ ID NO: 10 (see Table 2) is mature R160Q IFNγ. SEQ ID NO: 11 (see Table 2) is mature R160Q IFNγ without the propeptide. SEQ ID NO: 12 (MKYTSYILAFQLCIVLGSLGCYCQD-PYVQEAENLKKYFNAGHSDVADNGTLFLGILK NWKEESDRKIMQSQIVSFYFKLFKNFKD-DQSIQKSVETIKEDMNVKFFNSNKKKRDDF EKLT-NYSVTDLNVQRKAIHELIQVMAEL-SPAAKTGKRKRSQMLFQGRRASQ) is the full 166 amino acid sequence of K29Q and R160Q IFNγ. SEQ ID NO: 13 (see Table 2) is mature K29Q and R160Q IFNγ. SEQ ID NO: 14 (see Table 2) is mature K29Q and R160Q IFNγ without the propeptide.

Recombinant forms of IFNγ are available. Examples include, are not limited to, ACTIMMUNE™ (also known as IMUKIN™ and having SEQ ID NO: 2) available from Inter-Mune in Brisbane, Calif.; and recombinant human IFNγ cat. #300-02 (SEQ ID NO: 1) available from Peprotech in Rocky Hill, N.J.

Introduction of IFNγ into a variety of cell types modulates frataxin levels. Both frataxin mRNA and frataxin protein accumulate in response to IFNγ in frataxin-deficient cells lines, and frataxin is also in primary PBMC from FRDA patients. Frataxin is transcriptionally upregulated by IFNγ in multiple cellular systems, including frataxin-defective cells derived from FRDA patients.

In one embodiment, IFNγ is introduced into the cell in the form of a composition comprising a polypeptide having one or more of the sequences in Table 2. In one embodiment, the composition comprises a polypeptide having at least 75%, 80%, 85%, 90%, 95%, 98%, or 99% sequence identity to any one of the sequences in Table 2.

In one embodiment, IFNγ is administered to a patient in need of modulation of frataxin levels. In one embodiment, the patient has Friedreich's Ataxia. In one embodiment, the composition administered to the patient comprises a polypeptide having one or more of the sequences in Table 2. In one embodiment, the composition comprises a polypeptide having at least 75%, 80%, 85%, 90%, 95%, 98%, or 99% sequence identity to any one of the sequences in Table 2. In one embodiment, the composition administered to the patient further comprises mannitol, sodium succinate and polysorbate. In one embodiment the composition further comprises sterile water.

IFNγ can be administered to the patient through injection. In one embodiment, the patient is injected with a composition comprising 100 mcg of IFNγ formulated in 20 mg mannitol, 0.36 mg sodium succinate, 0.05 mg polysorbate 20 and sterile water for injection.

In one embodiment, ACTIMMUNE™ or IMUKIN™ (SEQ ID NO: 2) is administered to the patient according to the instructions on the packaging for the medication.

Modulation of Aconitase by Interferon Gamma

IFNγ upregulates the mitochondrial protein frataxin, a central component of the Fe/S clusters (ISC) machinery in eukaryotes (1, 14). The enzyme aconitase contains ISC. Frataxin deficiency therefore causes widespread metabolic disturbances, including severe reduction in mitochondrial ATP production, Kreb's cycle impairment and oxidative damage. Thus IFNγ-induced upregulation of frataxin in FRDA cells improves metabolic activity in the FRDA cells including recovery of aconitase activity.

Introducing IFNγ into cells results in improved aconitase activity. In one embodiment, IFNγ is introduced into the cell in the form of a composition comprising a polypeptide having one or more of the sequences in Table 2. In one embodiment, the composition comprises a polypeptide having at least 75%, 80%, 85%, 90%, 95%, 98%, or 99% sequence identity to any one of the sequences in Table 2.

In one embodiment, IFNγ is administered to a patient in need of improved aconitase activity. In one embodiment, the patient has Friedreich's Ataxia. In one embodiment, the composition administered to the patient comprises a polypeptide having one or more of the sequences in Table 2. In one embodiment, the composition comprises a polypeptide having at least 75%, 80%, 85%, 90%, 95%, 98%, or 99% sequence identity to any one of the sequences in Table 2. In one embodiment, the composition administered to the patient further comprises mannitol, sodium succinate and polysorbate. In one embodiment the composition further comprises sterile water.

IFNγ can be administered to the patient through injection. In one embodiment, the patient is injected with a composition comprising 100 mcg of IFNγ formulated in 20 mg mannitol, 0.36 mg sodium succinate, 0.05 mg polysorbate 20 and sterile water for injection.

In one embodiment, ACTIMMUNE™ or IMUKIN™ (SEQ ID NO: 2) is administered to the patient according to the instructions on the packaging for the medication.

EXAMPLES

General Procedures

Cell Cultures.

HeLa (human cervical carcinoma), U937 (monocytic leukemia), U118 (human glioblastoma) cell lines were obtained from the European cell culture collection. Hela and U937 cells were cultured in RPMI media supplemented with 10% fetal calf serum, 2 mM L-glutamine and antibiotics. U118 cells were cultured in D-MEM supplemented with 10% fetal bovine serum, 2 mM L-glutamine and antibiotics. Human peripheral blood mononuclear cells (PBMC), from healthy donors and FRDA patients, were isolated from heparinized venous blood by Ficoll-Type 400 gradient centrifugation. Human fibroblasts derived from a FRDA patient (GM03816) were obtained from the National Institute of General Medical Sciences (NIGMS) Human genetic Cell Repository at the Coriell Institute, Camden, N.J., USA. The cells were grown in DMEM 15% fetal calf serum with 2 mM L-glutamine and antibiotics. Recombinant human IFNγ was from Peprotech (cat. #300-02, seq.: MQDPYVKEAENLKKYFNAGHSD-VADNGTLFLGILKNWKEESDRKIMQSQIVSFYFKL FKNFKDDQSIQKSVETIKEDMNVKFFN-SNKKKRDDFEKLTNYSVTDLNVQRKAIHELI QVMAELSPAAKTGKRKRSQMLFQGRRASQ (SEQ ID NO:1)).

Immunoblotting.

Total cells extracts were prepared in ice cold RIPA lysis buffer supplemented with protease inhibitors. Proteins were separated on 12% SDS-PAGE, electroblotted on Protran nitrocellulose membranes (Whatman) and analyzed by ECL detection (GE Healthcare Life Sciences) with the following antibodies: mAb anti-frataxin (MAB-10876 Immunological sciences), mAb anti-alpha tubulin (Sigma), mAb anti-actin (Sigma).

Quantitative RT-PCR.

Total RNA (500 ng) isolated from FRDA fibroblasts was extracted using TRI-zol reagent (Invitrogen) and cDNA was then prepared by using SuperScript VILO (Invitrogen) according to the manufacturer's instructions. Levels of human FXN mRNA expression were assessed by quantitative RT-PCR using an ABI PrismÔ7000 sequencer and SYBR® Green (Applied Biosystems) with the following primers: RTFxnFWD 5'-CATACACGTTTGAGGACTATGATGTCT-3' and RTFxnREV 5'-TTCGGCGTCTGCTTGTTGATC-3' (Invitrogen) and Hs_ACTB_1_SG QuantiTect Primer Assay (200) (QT00095431) (Qiagen) for actin primers as housekeeping gene. Quantitative real time PCR analysis was carried out using the 2(-Delta Delta C(T)) method (2-DDCt). The data were normalized using the geometric mean of one housekeeping gene identified by geNorm 3.4 software (13). Fold change in gene expression was considered significantly different from reference when Student's t-test gave p<0.05.

Example 1

IFNγ Induces Frataxin Accumulation

To test whether IFNγ could affect frataxin protein levels, HeLa cells, U937 cells, U118 cells and peripheral blood mononuclear cells (PBMC) isolated from healthy donors were cultured for 24 hrs in the presence of the indicated concentrations of interferon gamma, then whole cell lysates were analyzed by SDS-PAGE and blotted with anti-frataxin and anti-actin mAbs. A minimum of three independent experiments for each cell type were performed. Representative blots are shown in FIG. 1. IFNγ induces the accumulation of frataxin in the human cervical carcinoma HeLa cells (FIG. 1A) and in the monocytic leukemia cell line U937 (FIG. 1B) in a dose-dependent manner. Similarly, IFNγ promoted frataxin expression in the human glioblastoma cell line U118 (FIG. 1C). To verify that IFNγ could induce frataxin accumulation in non transformed cells, resting peripheral blood mononuclear cells (PBMC) from normal individuals were exposed to IFNγ and frataxin accumulation quantitated by western blot. FIG. 1D shows that IFNγ induced frataxin accumulation in resting PBMC in a dose-dependent manner. Together these data indicate that IFNγ is capable to upregulate frataxin levels in a variety of cell types.

Example 2

IFNγ Induces Frataxin Expression in FRDA Cells

Figure 2:
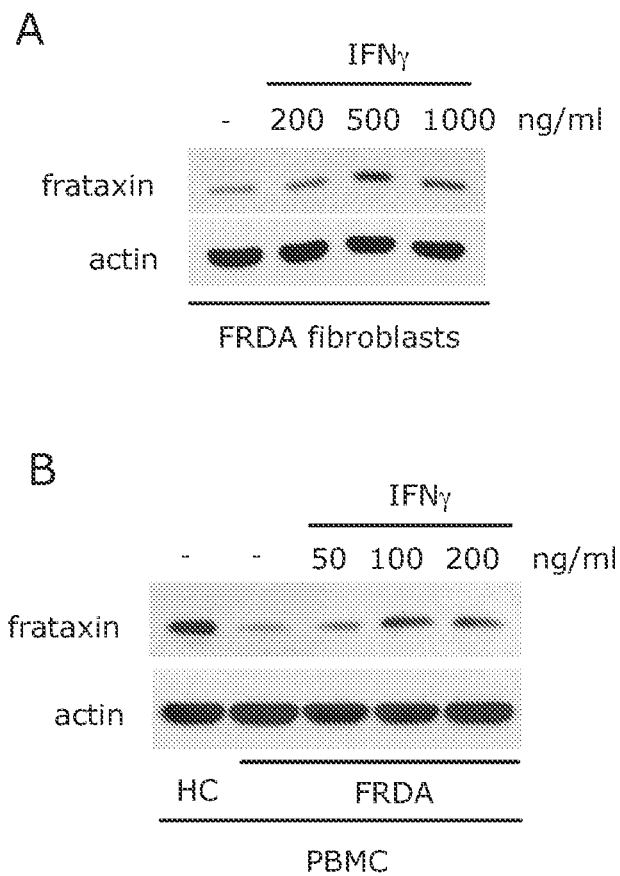
FIG. 2 Interferon gamma induces frataxin accumulation in FRDA cells.

FRDA-derived GM03816 fibroblasts were cultured for 24 hrs in the presence of the indicated concentrations of interferon gamma, then whole cell lysates were analyzed by SDS-PAGE and blotted with anti-frataxin and anti-actin mAbs. FIG. 2A shows a representative blot out of three independent experiments performed. As seen in FIG. 2A, IFNγ induced the upregulation of frataxin in frataxin-defective cells in a dose-dependent manner.

To verify that IFNγ could be effective on primary FRDA cells, peripheral blood mononuclear cells (PBMC) freshly isolated from an FRDA patient were cultured for 24 hrs in the presence of the indicated concentrations of Interferon gamma, then whole cell lysates were analyzed by SDS-PAGE and blotted with anti-frataxin and anti-actin mAbs. As shown in FIG. 2B IFNγ significantly increased frataxin expression in a dose dependent manner. The amount of frataxin present in the PBMC of a healthy brother of the patient is also shown for comparison (HC). The comparison indicates that IFNγ induced a recovery of up to ~50% of normal frataxin levels. PBMC isolated from nine out of ten FRDA patients (6 males and 4 females, GAA triplets range 350-915, age range 14-56) tested gave similar results.

Example 3

IFNγ Induces Frataxin mRNA Accumulation in FRDA Cells

Figure 3:
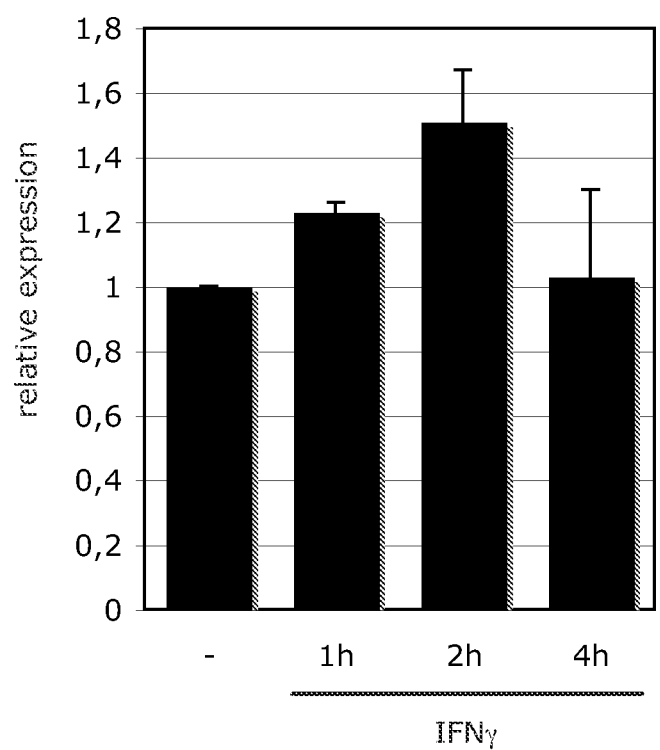
FIG. 3 Interferon gamma induces accumulation of frataxin mRNA in FRDA cells.

FRDA fibroblasts (GM03816 cells) were cultured for the indicated times in the presence of 500 ng/ml of Interferon gamma, then mRNA quantitated by RT-PCR. The means±1S.D. from three independent experiments are shown in FIG. 3. An increase in frataxin mRNA can be detected in FRDA fibroblasts as early as 1 hr after exposure to IFNγ, with peak accumulation at 2 hrs and return to baseline levels after 4 hrs. The increase in frataxin mRNA in IFNγ-treated cells, vs control-treated cells, was significant at 1 hr ($p<0.001$) and at 2 hrs ($p<0.05$). These results strongly suggest that IFNγ induces frataxin accumulation by increasing frataxin transcripts in FRDA cells.

Example 4

IFNγ Rescues the Aconitase Defect in FRDA Cells

Frataxin-defective cells have deficient activity of ISC-containing enzymes, such as aconitases. To investigate the functional consequences of IFNγ-induced frataxin upregulation, FRDA fibroblasts were cultured for 24 hrs in the presence of the indicated concentrations of IFNγ, then the enzymatic activity of aconitase was quantitated.

The FRDA fibroblasts were harvested by trypsinization, washed twice with ice-cold Dulbecco's Phosphate Buffered Saline (DPBS) and lysed in CelLytic M buffer (Sigma-Aldrich) supplemented with Complete protease inhibitor cocktail, EDTA-free (Roche). Aconitase activity was measured spectrophotometrically at 340 nm by a coupled reaction of aconitase and isocitrate dehydrogenase. The assay reactions contained 100 μg of cell extract in 50 mM Hepes pH 7.4, 1 mM sodium citrate, 0.6 mM $MnCl_2$, 0.2 mM $NADP^+$ and 2 U/ml isocitrate dehydrogenase (Sigma-Aldrich). For the calculation of enzymatic activitiy, one milliunit of enzyme was defined as the amount of protein that converted 1 nmol of $NADP^+$ in 1 min at 25° C. Statistical analysis was performed using a Student's t test; all values are expressed as means±1SD.

Figure 4:
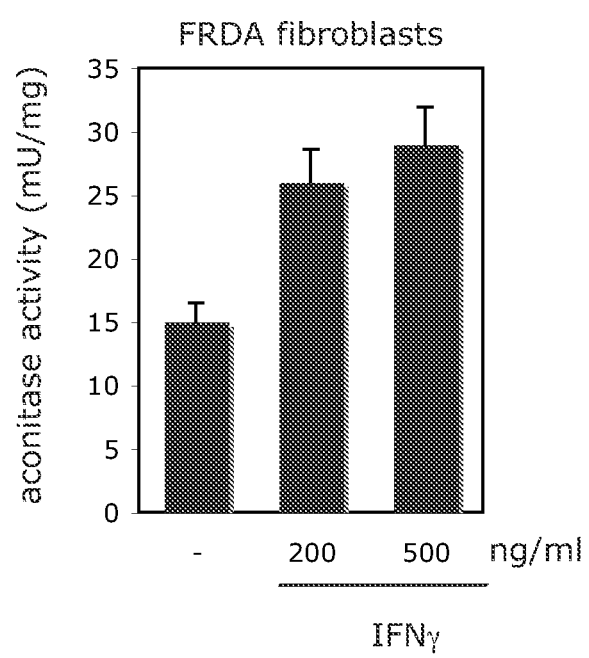
FIG. 4 Interferon gamma restores aconitase activity in FRDA cells.

The means±1S.D. from four independent experiments are shown in FIG. 4. The increase of aconitase activity in IFNγ-treated cells, vs control-treated cells, was significant ($p<0.01$) at both IFNγ concentrations. IFNγ induced a strong upregulation (up to >90% increase) of aconitase activity in FRDA fibroblasts.

Example 5

Figure 5:
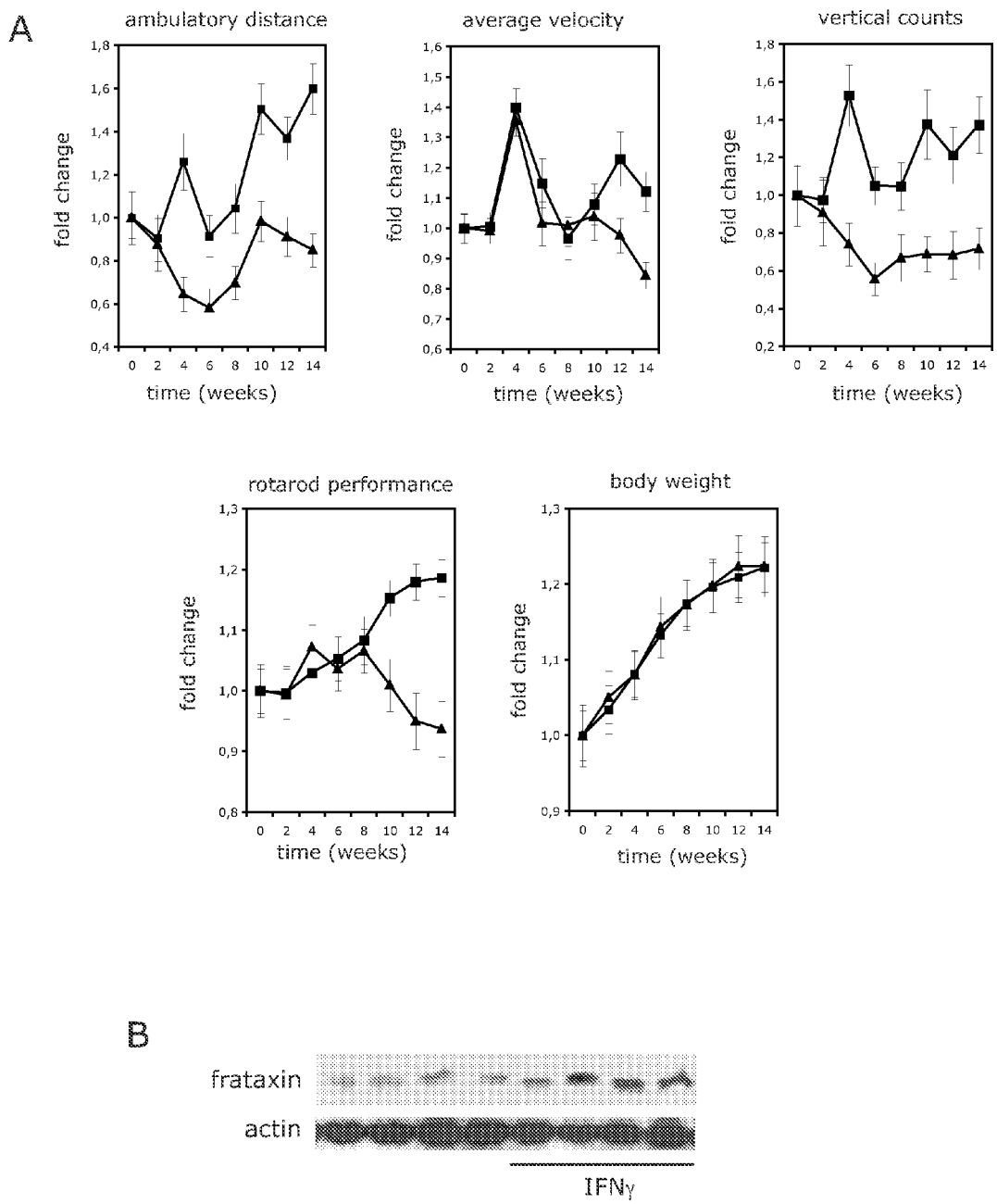
FIGS. 5A-5B Interferon gamma increases frataxin levels in vivo and improves locomotor and motor coordination in mice.

IFNγ Increases Frataxin Levels in Vivo and Improves Locomotor and Motor Coordination in Mice To investigate whether IFNγ could be effective in vivo, 13 FRDA mice (YG8R mice, engineered to express the human frataxin gene containing multiple GAA repeats (39,40)) were treated with subcutaneous injections of 40 μg/kg IFNγ, three times/week from 8 weeks of age for 14 weeks, while 13 FRDA mice of the same age were given vehicle. Every two weeks motor coordination and locomotor activity were assessed, including ambulatory distance, average velocity, vertical counts and rotarod performance. Body weight was also measured at every time point. As shown in FIG. 5A, FRDA mice treated with IFNγ displayed significantly enhanced locomotor activity, as measured by ambulatory distance ($p<0.01$), average velocity ($p<0.01$) and vertical counts ($p<0.001$), compared to vehicle-treated FRDA mice. Motor coordination, as measured by rotarod performance, improved dramatically in IFNγ-treated mice after 10 weeks of treatment compared to vehicle-treated mice ($p<0.001$). Better performances in locomotor activity and motor coordination in IFNγ-treated mice occurred independently of body weight changes. Mean fold change from time 0, ±s.e.m., for each parameter measured from 13 FRDA mice injected with IFNγ, compared to 13 FRDA mice injected with vehicle, is shown in FIG. 5A at the indicated time points. Squares: IFNγ-treated animals, triangles: vehicle-treated animals.

To verify that frataxin was in fact upregulated in vivo in IFNγ-responsive tissues, frataxin was quantitated in the spleen of 4 randomly-chosen FRDA mice treated with IFNγ and 4 randomly-chosen FRDA mice treated with vehicle at the end of the IFNγ treatment. Whole cell lysates were analyzed by SDS-PAGE and blotted with anti-frataxin and anti-actin mAbs. FIG. 5B shows that frataxin levels were indeed higher in the spleen of IFNγ-treated mice, compared to vehicle-treated FRDA mice.

Prophetic Example 1

Treatment of Friedreich's Ataxia with IFNγ

Recombinant IFNγ is produced in highly efficient protein expression systems, purified and administered to an animal having reduced frataxin or having Friedreich's Ataxia (FRDA). IFNγ is administered in a monomeric or dimeric form, formulated with an appropriate excipient. A dose of 1-2 million IU IFNγ/m² of body surface is injected subcutaneously or intramuscularly on an every other day schedule, or three times per week. Alternative regimens or administration routes are followed where appropriate.

Animals are monitored during treatment by standard laboratory procedures for accumulation of frataxin in peripheral blood mononuclear cells (e.g., by SDS-PAGE followed by immunoblot analysis of cellular lysates, by intracellular immunostaining, and/or by FACS analysis of intact cells). Treatment with recombinant IFNγ causes an increase of cellular frataxin levels in frataxin-deficient animals.

Prophetic Example 2

Treatment of Friedreich's Ataxia with IFNγ

Recombinant IFNγ is produced in highly efficient protein expression systems, purified and administered to a patient diagnosed as having Friedreich's Ataxia (FRDA). IFNγ is administered in a monomeric or dimeric form, formulated with an appropriate excipient. A dose of 1-2 million IU IFNγ/m² of body surface is injected subcutaneously or intramuscularly on an every other day schedule, or three times per week. Alternative regimens or administration routes are followed where appropriate.

Treatment with recombinant IFNγ is started after diagnosis of FRDA has been established. For one experimental data set, FRDA patients that have already undergone unsatisfactory therapy are injected with recombinant IFNγ after the minimal necessary washout period. Patients are monitored during treatment by standard clinical/laboratory procedures (e.g., physical examination, ECG, hematochemical analysis, recording of possible adverse side effects), for accumulation of frataxin in peripheral blood mononuclear cells (e.g., by SDS-PAGE followed by immunoblot analysis of cellular lysates, by intracellular immunostaining, and/or by FACS analysis of intact cells), and for specific efficacy parameters, as quantitated by scales such as the International Cooperative Ataxia Rating Scale (ICARS), the Friedreich's Ataxia Rating Scale (FARS), the Modified Berthel Index (MBI) or the Functional Independence Measure (FIM). Treatment with recombinant IFNγ causes an increase of cellular frataxin levels in FRDA patients, and a consequent amelioration of the clinical parameters, as is measured by one or more of the above mentioned scoring methods.

In addition, recombinant IFNγ is used in FRDA patients together with other therapeutic approaches (e.g., antioxidants-based treatments) using optimal combination regimens. Again, combination treatment with recombinant IFNγ causes an additional increase of cellular frataxin levels, and a consequent amelioration of the clinical parameters, as is measured by at least one of the ICARS, FARS, MBI or FIM scores.

The description herein has been presented for the purpose of illustration; it is not intended to be exhaustive or to limit the invention to the precise forms disclosed. Persons skilled in the relevant art can appreciate that many modifications and variations are possible in light of the teachings.

It should be noted that the language used in the description has been principally selected for readability and instructional purposes, and it may not have been selected to delineate or circumscribe the inventive subject matter. Accordingly, the disclosure of the following description is intended to be illustrative, but not limiting, of the scope of the invention.

TABLE 2

| | |
|---|---|
| SEQ ID NO: 1 | MQDPYVKEAENLKKYFNAGHSDVADNGTLFLGILKNWKEESDR KIMQSQIVSFYFKLFKNFKDDQSIQKSVETIKEDMNVKFFNSNKKK RDDFEKLTNYSVTDLNVQRKAIHELIQVMAELSPAAKTGKRKRSQ MLFQGRRASQ |
| SEQ ID NO: 2 | MQDPYVKEAENLKKYFNAGHSDVADNGTLFLGILKNWKEESDR KIMQSQIVSFYFKLFKNFKDDQSIQKSVETIKEDMNVKFFNSNKKK RDDFEKLTNYSVTDLNVQRKAIHELIQVMAELSPAAKTGKRKRSQ MLFRGR |
| SEQ ID NO: 4 | QDPYVKEAENLKKYFNAGHSDVADNGTLFLGILKNWKEESDRKI MQSQIVSFYFKLFKNFKDDQSIQKSVETIKEDMNVKFFNSNKKKR DDFEKLTNYSVTDLNVQRKAIHELIQVMAELSPAAKTGKRKRSQ MLFR GRRASQ |
| SEQ ID NO: 5 | QDPYVKEAENLKKYFNAGHSDVADNGTLFLGILKNWKEESDRKI MQSQIVSFYFKLFKNFKDDQSIQKSVETIKEDMNVKFFNSNKKKR DDFEKLTNYSVTDLNVQRKAIHELIQVMAELSPAAKTGKRKRSQ MLFRG |
| SEQ ID NO: 7 | QDPYVQEAENLKKYFNAGHSDVADNGTLFLGILKNWKEESDRKI MQSQIVSFYFKLFKNFKDDQSIQKSVETIKEDMNVKFFNSNKKKR DDFEKLTNYSVTDLNVQRKAIHELIQVMAELSPAAKTGKRKRSQ MLFRGRRASQ |
| SEQ ID NO: 8 | QDPYVQEAENLKKYFNAGHSDVADNGTLFLGILKNWKEESDRKI MQSQIVSFYFKLFKNFKDDQSIQKSVETIKEDMNVKFFNSNKKKR DDFEKLTNYSVTDLNVQRKAIHELIQVMAELSPAAKTGKRKRSQ MLFRG |
| SEQ ID NO: 10 | QDPYVKEAENLKKYFNAGHSDVADNGTLFLGILKNWKEESDRKI MQSQIVSFYFKLFKNFKDDQSIQKSVETIKEDMNVKFFNSNKKKR DDFEKLTNYSVTDLNVQRKAIHELIQVMAELSPAAKTGKRKRSQ MLFQGRRASQ |
| SEQ ID NO: 11 | QDPYVKEAENLKKYFNAGHSDVADNGTLFLGILKNWKEESDRKI MQSQIVSFYFKLFKNFKDDQSIQKSVETIKEDMNVKFFNSNKKKR |

TABLE 2-continued

```
                DDFEKLTNYSVTDLNVQRKAIHELIQVMAELSPAAKTGKRKRSQ
                MLFQG

SEQ ID NO: 13   QDPYVQEAENLKKYFNAGHSDVADNGTLFLGILKNWKEESDRKI
                MQSQIVSFYFKLFKNFKDDQSIQKSVETIKEDMNVKFFNSNKKKR
                DDFEKLTNYSVTDLNVQRKAIHELIQVMAELSPAAKTGKRKRSQ
                MLFQGRRASQ

SEQ ID NO: 14   QDPYVQEAENLKKYFNAGHSDVADNGTLFLGILKNWKEESDRKI
                MQSQIVSFYFKLFKNFKDDQSIQKSVETIKEDMNVKFFNSNKKKR
                DDFEKLTNYSVTDLNVQRKAIHELIQVMAELSPAAKTGKRKRSQ
                MLFQG
```

REFERENCES

1. Pandolfo, M., and A. Pastore. 2009. The pathogenesis of Friedreich ataxia and the structure and function of frataxin. *J Neurol* 256 Suppl 1:9-17.
2. Pandolfo, M. 2009. Friedreich ataxia: the clinical picture. *J Neurol* 256 Suppl 1:3-8.
3. Delatycki, M. B. 2009. Evaluating the progression of Friedreich ataxia and its treatment. *J Neurol* 256 Suppl 1:36-41.
4. Marmolino, D., and F. Acquaviva. 2009. Friedreich's Ataxia: from the (GAA)n repeat mediated silencing to new promising molecules for therapy. *Cerebellum* 8:245-259.
5. Puccio, H. 2009. Multicellular models of Friedreich ataxia. *J Neurol* 256 Suppl 1:18-24.
6. Condò, I., N. Ventura, F. Malisan, A. Rufini, B. Tomassini, and R. Testi. 2007. In vivo maturation of human frataxin. *Hum Mol Genet* 16:1534-1540.
7. Schmucker, S., M. Argentini, N. Carelle-Calmels, A. Martelli, and H. Puccio. 2008. The in vivo mitochondrial two-step maturation of human frataxin. *Hum Mol Genet* 17:3521-3531.
8. Acquaviva, F., I. De Biase, L. Nezi, G. Ruggiero, F. Tatangelo, C. Pisano, A. Monticelli, C. Garbi, A. M. Acquaviva, and S. Cocozza. 2005. Extra-mitochondrial localisation of frataxin and its association with IscU1 during enterocyte-like differentiation of the human colon adenocarcinoma cell line Caco-2. *J Cell Sci* 118:3917-3924.
9. Condò, I., N. Ventura, F. Malisan, B. Tomassini, and R. Testi. 2006. A pool of extramitochondrial frataxin that promotes cell survival. *J Biol Chem* 281:16750-16756.
10. Condò, I., F. Malisan, I. Guccini, D. Serio, A. Rufini, and R. Testi. 2010. Molecular control of the cytosolic aconitase/IRP1 switch by extramitochondrial frataxin. *Hum Mol Genet* 19:1221-1229.
11. Yoon, T., and J. A. Cowan. 2003. Iron-sulfur cluster biosynthesis. Characterization of frataxin as an iron donor for assembly of [2Fe-2S] clusters in ISU-type proteins. *J Am Chem Soc* 125:6078-6084.
12. Adinolfi, S., C. Iannuzzi, F. Prischi, C. Pastore, S. Iametti, S. R. Martin, F. Bonomi, and A. Pastore. 2009. Bacterial frataxin CyaY is the gatekeeper of iron-sulfur cluster formation catalyzed by IscS. *Nat Struct Mol Biol* 16:390-396.
13. Vandesompele, J., K. De Preter, F. Pattyn, B. Poppe, N. Van Roy, A. De Paepe, and F. Speleman. 2002. Accurate normalization of real-time quantitative RT-PCR data by geometric averaging of multiple internal control genes. *Genome Biol* 3:RESEARCH0034.
14. Stemmler, T. L., E. Lesuisse, D. Pain, and A. Dancis. 2010. Frataxin and mitochondrial Fe-S cluster biogenesis. *J Biol Chem*
15. Lill, R., and U. Muhlenhoff. 2006. Iron-sulfur protein biogenesis in eukaryotes: components and mechanisms. *Annu Rev Cell Dev Biol* 22:457-486.
16. Bandyopadhyay, S., K. Chandramouli, and M. K. Johnson. 2008. Iron-sulfur cluster biosynthesis. *Biochem Soc Trans* 36:1112-1119.
17. Collins, H. L. 2008. Withholding iron as a cellular defence mechanism—friend or foe? *Eur J Immunol* 38:1803-1806.
18. Ganz, T. 2009. Iron in innate immunity: starve the invaders. *Curr Opin Immunol* 21:63-67.
19. Byrd, T. F., and M. A. Horwitz. 1993. Regulation of transferrin receptor expression and ferritin content in human mononuclear phagocytes. Coordinate upregulation by iron transferrin and downregulation by interferon gamma. *J Clin Invest* 91:969-976.
20. Feelders, R. A., G. Vreugdenhil, A. M. Eggermont, P. A. Kuiper-Kramer, H. G. van Eijk, and A. J. Swaak. 1998. Regulation of iron metabolism in the acute-phase response: interferon gamma and tumour necrosis factor alpha induce hypoferraemia, ferritin production and a decrease in circulating transferrin receptors in cancer patients. *Eur J Clin Invest* 28:520-527.
21. Tacchini, L., E. Gammella, C. De Ponti, S. Recalcati, and G. Cairo. 2008. Role of HIF-1 and NF-kappaB transcription factors in the modulation of transferrin receptor by inflammatory and anti-inflammatory signals. *J Biol Chem* 283:20674-20686.
22. Ludwiczek, S., E. Aigner, I. Theurl, and G. Weiss. 2003. Cytokine-mediated regulation of iron transport in human monocytic cells. *Blood* 101:4148-4154.
23. Van Zandt, K. E., F. B. Sow, W. C. Florence, B. S. Zwilling, A. R. Satoskar, L. S. Schlesinger, and W. P. Lafuse. 2008. The iron export protein ferroportin 1 is differentially expressed in mouse macrophage populations and is present in the mycobacterial-containing phagosome. *J Leukoc Biol* 84:689-700.
24. Sow, F. B., W. C. Florence, A. R. Satoskar, L. S. Schlesinger, B. S. Zwilling, and W. P. Lafuse. 2007. Expression and localization of hepcidin in macrophages: a role in host defense against tuberculosis. *J Leukoc Biol* 82:934-945.
25. Kim, S., and P. Ponka. 2000. Effects of interferon-gamma and lipopolysaccharide on macrophage iron metabolism are mediated by nitric oxide-induced degradation of iron regulatory protein 2. *J Biol Chem* 275:6220-6226.
26. Alter-Koltunoff, M., S. Goren, J. Nousbeck, C. G. Feng, A. Sher, K. Ozato, A. Azriel, and B. Z. Levi. 2008. Innate immunity to intraphagosomal pathogens is mediated by interferon regulatory factor 8 (IRF-8) that stimulates the expression of macrophage-specific Nramp1 through antagonizing repression by c-Myc. *J Biol Chem* 283:2724-2733.

27. Richardson, D. R., M. L. Huang, M. Whitnall, E. M. Becker, P. Ponka, and Y. S. Rahmanto. 2010. The ins and outs of mitochondrial iron-loading: the metabolic defect in Friedreich's ataxia. *J Mol Med* 88:323-329.
28. Saha, B., S. Jyothi Prasanna, B. Chandrasekar, and D. Nandi. 2010. Gene modulation and immunoregulatory roles of interferon gamma. *Cytokine* 50:1-14.
29. Vanin, A. F. 2009. Dinitrosyl iron complexes with thiolate ligands: physico-chemistry, biochemistry and physiology. *Nitric Oxide* 21:1-13.
30. Castro, L., M. Rodriguez, and R. Radi. 1994. Aconitase is readily inactivated by peroxynitrite, but not by its precursor, nitric oxide. *J Biol Chem* 269:29409-29415.
31. Kennedy, M. C., W. E. Antholine, and H. Beinert. 1997. An EPR investigation of the products of the reaction of cytosolic and mitochondrial aconitases with nitric oxide. *J Biol Chem* 272:20340-20347.
32. Tsou, A. Y., L. S. Friedman, R. B. Wilson, and D. R. Lynch. 2009. Pharmacotherapy for Friedreich ataxia. *CNS Drugs* 23:213-223.
33. Marmolino, D., M. Manto, F. Acquaviva, P. Vergara, A. Ravella, A. Monticelli, and M. Pandolfo. 2010. PGC-1alpha down-regulation affects the antioxidant response in Friedreich's ataxia. *PLoS One* 5:e10025.
34. Sturm, B., D. Stupphann, C. Kaun, S. Boesch, M. Schranzhofer, J. Wojta, H. Goldenberg, and B. Scheiber-Mojdehkar. 2005. Recombinant human erythropoietin: effects on frataxin expression in vitro. *Eur J Clin Invest* 35:711-717.
35. Acquaviva, F., I. Castaldo, A. Filla, M. Giacchetti, D. Marmolino, A. Monticelli, M. Pinelli, F. Sacca, and S. Cocozza. 2008. Recombinant human erythropoietin increases frataxin protein expression without increasing mRNA expression. *Cerebellum* 7:360-365.
36. Herman, D., K. Jenssen, R. Burnett, E. Soragni, S. L. Perlman, and J. M. Gottesfeld. 2006. Histone deacetylase inhibitors reverse gene silencing in Friedreich's ataxia. *Nat Chem Biol* 2:551-558.
37. Rai, M., E. Soragni, K. Jenssen, R. Burnett, D. Herman, G. Coppola, D. H. Geschwind, J. M. Gottesfeld, and M. Pandolfo. 2008. HDAC inhibitors correct frataxin deficiency in a Friedreich ataxia mouse model. *PLoS One* 3:e1958.
38. Miller, C. H., S. G. Maher, and H. A. Young. 2009. Clinical Use of Interferon-gamma. *Ann N Y Acad Sci* 1182:69-79.
39. Al-Mandawi, S., et al. The Friedreich ataxia GAA repeat expansion mutation induces comparable epigenetic changes in human and transgenic mouse brain and heart tissues. *Hum Mol Genet* 17, 735-746 (2008).
40. Al-Mandawi, S., et al. GAA repeat expansion mutation mouse models of Friedreich ataxia exhibit oxidative stress leading to progressive neuronal and cardiac pathology. *Genomics* 88, 580-590 (2006).

---

What is claimed is:

1. A method of increasing expression of frataxin in a cell, comprising identifying a cell having a deficient amount of frataxin, or from a subject diagnosed as having Friedreich's Ataxia, comprising administering an effective amount of interferon gamma to said cell.

2. The method of claim 1 wherein said interferon gamma is recombinant.

3. The method of claim 1 wherein said interferon gamma consists of or comprises a polypeptide having an amino acid sequence selected from the group consisting of SEQ ID NO: 1, 2, 4, 5, 7, 8, 10, 11, 13 and 14.

4. The method of claim 1 wherein said interferon gamma is a polypeptide having the amino acid sequence of SEQ ID NO: 2.

5. The method of claim 1 wherein said interferon gamma consists of or comprises a polypeptide having the amino acid sequence of SEQ ID NO: 2.

6. A method of treating Friedreich's Ataxia, comprising administering to a subject diagnosed as having Friedreich's Ataxia a therapeutically effective amount of interferon gamma.

7. The method of claim 6, wherein said interferon gamma is recombinant.

8. The method of claim 6 wherein said interferon gamma consists of or comprises a polypeptide having an amino acid sequence selected from the group consisting of SEQ ID NO: 1, 2, 4, 5, 7, 8, 10, 11, 13 and 14.

9. The method of claim 6 wherein said interferon gamma is a polypeptide having the amino acid sequence of SEQ ID NO: 2.

10. The method of claim 6 wherein said interferon gamma consists of or comprises a polypeptide having the amino acid sequence of SEQ ID NO: 2.

11. A method of upregulating frataxin, comprising administering to a subject in need thereof a therapeutically effective amount of interferon gamma.

12. The method of claim 11, wherein said interferon gamma is recombinant.

13. The method of claim 11 wherein said interferon gamma consists of or comprises a polypeptide having an amino acid sequence selected from the group consisting of SEQ ID NO: 1, 2, 4, 5, 7, 8, 10, 11, 13 and 14.

14. The method of claim 11 wherein said interferon gamma is a polypeptide having the amino acid sequence of SEQ ID NO: 2.

15. The method of claim 11 wherein said interferon gamma consists of or comprises a polypeptide having the amino acid sequence of SEQ ID NO: 2.

* * * * *

SEQUENCE LISTING

```
<160> NUMBER OF SEQ ID NOS: 16

<210> SEQ ID NO 1
<211> LENGTH: 144
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 1

Met Gln Asp Pro Tyr Val Lys Glu Ala Glu Asn Leu Lys Lys Tyr Phe
1               5                   10                  15

Asn Ala Gly His Ser Asp Val Ala Asp Asn Gly Thr Leu Phe Leu Gly
            20                  25                  30

Ile Leu Lys Asn Trp Lys Glu Glu Ser Asp Arg Lys Ile Met Gln Ser
        35                  40                  45

Gln Ile Val Ser Phe Tyr Phe Lys Leu Phe Lys Asn Phe Lys Asp Asp
    50                  55                  60

Gln Ser Ile Gln Lys Ser Val Glu Thr Ile Lys Glu Asp Met Asn Val
65                  70                  75                  80

Lys Phe Phe Asn Ser Asn Lys Lys Lys Arg Asp Asp Phe Glu Lys Leu
                85                  90                  95

Thr Asn Tyr Ser Val Thr Asp Leu Asn Val Gln Arg Lys Ala Ile His
            100                 105                 110

Glu Leu Ile Gln Val Met Ala Glu Leu Ser Pro Ala Ala Lys Thr Gly
        115                 120                 125

Lys Arg Lys Arg Ser Gln Met Leu Phe Gln Gly Arg Arg Ala Ser Gln
    130                 135                 140

<210> SEQ ID NO 2
<211> LENGTH: 140
<212> TYPE: PRT
```

<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 2

Met Gln Asp Pro Tyr Val Lys Glu Ala Glu Asn Leu Lys Lys Tyr Phe
1               5                   10                  15

Asn Ala Gly His Ser Asp Val Ala Asp Asn Gly Thr Leu Phe Leu Gly
            20                  25                  30

Ile Leu Lys Asn Trp Lys Glu Glu Ser Asp Arg Lys Ile Met Gln Ser
        35                  40                  45

Gln Ile Val Ser Phe Tyr Phe Lys Leu Phe Lys Asn Phe Lys Asp Asp
    50                  55                  60

Gln Ser Ile Gln Lys Ser Val Glu Thr Ile Lys Glu Asp Met Asn Val
65                  70                  75                  80

Lys Phe Phe Asn Ser Asn Lys Lys Arg Asp Asp Phe Glu Lys Leu
                85                  90                  95

Thr Asn Tyr Ser Val Thr Asp Leu Asn Val Gln Arg Lys Ala Ile His
            100                 105                 110

Glu Leu Ile Gln Val Met Ala Glu Leu Ser Pro Ala Ala Lys Thr Gly
        115                 120                 125

Lys Arg Lys Arg Ser Gln Met Leu Phe Arg Gly Arg
    130                 135                 140

<210> SEQ ID NO 3
<211> LENGTH: 166
<212> TYPE: PRT
<213> ORGANISM: Homo sapiens

<400> SEQUENCE: 3

Met Lys Tyr Thr Ser Tyr Ile Leu Ala Phe Gln Leu Cys Ile Val Leu
1               5                   10                  15

Gly Ser Leu Gly Cys Tyr Cys Gln Asp Pro Tyr Val Lys Glu Ala Glu
            20                  25                  30

Asn Leu Lys Lys Tyr Phe Asn Ala Gly His Ser Asp Val Ala Asp Asn
        35                  40                  45

Gly Thr Leu Phe Leu Gly Ile Leu Lys Asn Trp Lys Glu Glu Ser Asp
    50                  55                  60

Arg Lys Ile Met Gln Ser Gln Ile Val Ser Phe Tyr Phe Lys Leu Phe
65                  70                  75                  80

Lys Asn Phe Lys Asp Asp Gln Ser Ile Gln Lys Ser Val Glu Thr Ile
                85                  90                  95

Lys Glu Asp Met Asn Val Lys Phe Phe Asn Ser Asn Lys Lys Lys Arg
            100                 105                 110

Asp Asp Phe Glu Lys Leu Thr Asn Tyr Ser Val Thr Asp Leu Asn Val
        115                 120                 125

Gln Arg Lys Ala Ile His Glu Leu Ile Gln Val Met Ala Glu Leu Ser
    130                 135                 140

Pro Ala Ala Lys Thr Gly Lys Arg Lys Arg Ser Gln Met Leu Phe Arg
145                 150                 155                 160

Gly Arg Arg Ala Ser Gln
                165

<210> SEQ ID NO 4
<211> LENGTH: 143

```
<212> TYPE: PRT
<213> ORGANISM: Homo sapiens

<400> SEQUENCE: 4

Gln Asp Pro Tyr Val Lys Glu Ala Glu Asn Leu Lys Lys Tyr Phe Asn
1               5                   10                  15

Ala Gly His Ser Asp Val Ala Asp Asn Gly Thr Leu Phe Leu Gly Ile
            20                  25                  30

Leu Lys Asn Trp Lys Glu Glu Ser Asp Arg Lys Ile Met Gln Ser Gln
        35                  40                  45

Ile Val Ser Phe Tyr Phe Lys Leu Phe Lys Asn Phe Lys Asp Asp Gln
    50                  55                  60

Ser Ile Gln Lys Ser Val Glu Thr Ile Lys Glu Asp Met Asn Val Lys
65                  70                  75                  80

Phe Phe Asn Ser Asn Lys Lys Arg Asp Asp Phe Glu Lys Leu Thr
                85                  90                  95

Asn Tyr Ser Val Thr Asp Leu Asn Val Gln Arg Lys Ala Ile His Glu
            100                 105                 110

Leu Ile Gln Val Met Ala Glu Leu Ser Pro Ala Ala Lys Thr Gly Lys
        115                 120                 125

Arg Lys Arg Ser Gln Met Leu Phe Arg Gly Arg Arg Ala Ser Gln
    130                 135                 140

<210> SEQ ID NO 5
<211> LENGTH: 138
<212> TYPE: PRT
<213> ORGANISM: Homo sapiens

<400> SEQUENCE: 5

Gln Asp Pro Tyr Val Lys Glu Ala Glu Asn Leu Lys Lys Tyr Phe Asn
1               5                   10                  15

Ala Gly His Ser Asp Val Ala Asp Asn Gly Thr Leu Phe Leu Gly Ile
            20                  25                  30

Leu Lys Asn Trp Lys Glu Glu Ser Asp Arg Lys Ile Met Gln Ser Gln
        35                  40                  45

Ile Val Ser Phe Tyr Phe Lys Leu Phe Lys Asn Phe Lys Asp Asp Gln
    50                  55                  60

Ser Ile Gln Lys Ser Val Glu Thr Ile Lys Glu Asp Met Asn Val Lys
65                  70                  75                  80

Phe Phe Asn Ser Asn Lys Lys Arg Asp Asp Phe Glu Lys Leu Thr
                85                  90                  95

Asn Tyr Ser Val Thr Asp Leu Asn Val Gln Arg Lys Ala Ile His Glu
            100                 105                 110

Leu Ile Gln Val Met Ala Glu Leu Ser Pro Ala Ala Lys Thr Gly Lys
        115                 120                 125

Arg Lys Arg Ser Gln Met Leu Phe Arg Gly
    130                 135

<210> SEQ ID NO 6
<211> LENGTH: 166
<212> TYPE: PRT
<213> ORGANISM: Homo sapiens

<400> SEQUENCE: 6

Met Lys Tyr Thr Ser Tyr Ile Leu Ala Phe Gln Leu Cys Ile Val Leu
1               5                   10                  15

Gly Ser Leu Gly Cys Tyr Cys Gln Asp Pro Tyr Val Gln Glu Ala Glu
```

```
            20                  25                  30

Asn Leu Lys Lys Tyr Phe Asn Ala Gly His Ser Asp Val Ala Asp Asn
        35                  40                  45

Gly Thr Leu Phe Leu Gly Ile Leu Lys Asn Trp Lys Glu Glu Ser Asp
    50                  55                  60

Arg Lys Ile Met Gln Ser Gln Ile Val Ser Phe Tyr Phe Lys Leu Phe
65                  70                  75                  80

Lys Asn Phe Lys Asp Asp Gln Ser Ile Gln Lys Ser Val Glu Thr Ile
                85                  90                  95

Lys Glu Asp Met Asn Val Lys Phe Phe Asn Ser Asn Lys Lys Lys Arg
            100                 105                 110

Asp Asp Phe Glu Lys Leu Thr Asn Tyr Ser Val Thr Asp Leu Asn Val
        115                 120                 125

Gln Arg Lys Ala Ile His Glu Leu Ile Gln Val Met Ala Glu Leu Ser
    130                 135                 140

Pro Ala Ala Lys Thr Gly Lys Arg Lys Arg Ser Gln Met Leu Phe Arg
145                 150                 155                 160

Gly Arg Arg Ala Ser Gln
                165

<210> SEQ ID NO 7
<211> LENGTH: 143
<212> TYPE: PRT
<213> ORGANISM: Homo sapiens

<400> SEQUENCE: 7

Gln Asp Pro Tyr Val Gln Glu Ala Glu Asn Leu Lys Lys Tyr Phe Asn
1               5                   10                  15

Ala Gly His Ser Asp Val Ala Asp Asn Gly Thr Leu Phe Leu Gly Ile
            20                  25                  30

Leu Lys Asn Trp Lys Glu Glu Ser Asp Arg Lys Ile Met Gln Ser Gln
        35                  40                  45

Ile Val Ser Phe Tyr Phe Lys Leu Phe Lys Asn Phe Lys Asp Asp Gln
    50                  55                  60

Ser Ile Gln Lys Ser Val Glu Thr Ile Lys Glu Asp Met Asn Val Lys
65                  70                  75                  80

Phe Phe Asn Ser Asn Lys Lys Lys Arg Asp Asp Phe Glu Lys Leu Thr
                85                  90                  95

Asn Tyr Ser Val Thr Asp Leu Asn Val Gln Arg Lys Ala Ile His Glu
            100                 105                 110

Leu Ile Gln Val Met Ala Glu Leu Ser Pro Ala Ala Lys Thr Gly Lys
        115                 120                 125

Arg Lys Arg Ser Gln Met Leu Phe Arg Gly Arg Arg Ala Ser Gln
    130                 135                 140

<210> SEQ ID NO 8
<211> LENGTH: 138
<212> TYPE: PRT
<213> ORGANISM: Homo sapiens

<400> SEQUENCE: 8

Gln Asp Pro Tyr Val Gln Glu Ala Glu Asn Leu Lys Lys Tyr Phe Asn
1               5                   10                  15

Ala Gly His Ser Asp Val Ala Asp Asn Gly Thr Leu Phe Leu Gly Ile
            20                  25                  30

Leu Lys Asn Trp Lys Glu Glu Ser Asp Arg Lys Ile Met Gln Ser Gln
```

```
            35                  40                  45
Ile Val Ser Phe Tyr Phe Lys Leu Phe Lys Asn Phe Lys Asp Asp Gln
        50                  55                  60

Ser Ile Gln Lys Ser Val Glu Thr Ile Lys Glu Asp Met Asn Val Lys
65                  70                  75                  80

Phe Phe Asn Ser Asn Lys Lys Lys Arg Asp Asp Phe Glu Lys Leu Thr
                85                  90                  95

Asn Tyr Ser Val Thr Asp Leu Asn Val Gln Arg Lys Ala Ile His Glu
            100                 105                 110

Leu Ile Gln Val Met Ala Glu Leu Ser Pro Ala Ala Lys Thr Gly Lys
        115                 120                 125

Arg Lys Arg Ser Gln Met Leu Phe Arg Gly
130                 135
```

<210> SEQ ID NO 9
<211> LENGTH: 166
<212> TYPE: PRT
<213> ORGANISM: Homo sapiens

<400> SEQUENCE: 9

```
Met Lys Tyr Thr Ser Tyr Ile Leu Ala Phe Gln Leu Cys Ile Val Leu
1               5                   10                  15

Gly Ser Leu Gly Cys Tyr Cys Gln Asp Pro Tyr Val Lys Glu Ala Glu
            20                  25                  30

Asn Leu Lys Lys Tyr Phe Asn Ala Gly His Ser Asp Val Ala Asp Asn
        35                  40                  45

Gly Thr Leu Phe Leu Gly Ile Leu Lys Asn Trp Lys Glu Glu Ser Asp
    50                  55                  60

Arg Lys Ile Met Gln Ser Gln Ile Val Ser Phe Tyr Phe Lys Leu Phe
65                  70                  75                  80

Lys Asn Phe Lys Asp Asp Gln Ser Ile Gln Lys Ser Val Glu Thr Ile
                85                  90                  95

Lys Glu Asp Met Asn Val Lys Phe Phe Asn Ser Asn Lys Lys Lys Arg
            100                 105                 110

Asp Asp Phe Glu Lys Leu Thr Asn Tyr Ser Val Thr Asp Leu Asn Val
        115                 120                 125

Gln Arg Lys Ala Ile His Glu Leu Ile Gln Val Met Ala Glu Leu Ser
    130                 135                 140

Pro Ala Ala Lys Thr Gly Lys Arg Lys Arg Ser Gln Met Leu Phe Gln
145                 150                 155                 160

Gly Arg Arg Ala Ser Gln
                165
```

<210> SEQ ID NO 10
<211> LENGTH: 143
<212> TYPE: PRT
<213> ORGANISM: Homo sapiens

<400> SEQUENCE: 10

```
Gln Asp Pro Tyr Val Lys Glu Ala Glu Asn Leu Lys Lys Tyr Phe Asn
1               5                   10                  15

Ala Gly His Ser Asp Val Ala Asp Asn Gly Thr Leu Phe Leu Gly Ile
            20                  25                  30

Leu Lys Asn Trp Lys Glu Glu Ser Asp Arg Lys Ile Met Gln Ser Gln
        35                  40                  45

Ile Val Ser Phe Tyr Phe Lys Leu Phe Lys Asn Phe Lys Asp Asp Gln
```

```
Ser Ile Gln Lys Ser Val Glu Thr Ile Lys Glu Asp Met Asn Val Lys
 65                  70                  75                  80

Phe Phe Asn Ser Asn Lys Lys Arg Asp Asp Phe Glu Lys Leu Thr
                 85                  90                  95

Asn Tyr Ser Val Thr Asp Leu Asn Val Gln Arg Lys Ala Ile His Glu
                100                 105                 110

Leu Ile Gln Val Met Ala Glu Leu Ser Pro Ala Ala Lys Thr Gly Lys
            115                 120                 125

Arg Lys Arg Ser Gln Met Leu Phe Gln Gly Arg Arg Ala Ser Gln
        130                 135                 140
```

<210> SEQ ID NO 11
<211> LENGTH: 138
<212> TYPE: PRT
<213> ORGANISM: Homo sapiens

<400> SEQUENCE: 11

```
Gln Asp Pro Tyr Val Lys Glu Ala Glu Asn Leu Lys Lys Tyr Phe Asn
 1               5                  10                  15

Ala Gly His Ser Asp Val Ala Asp Asn Gly Thr Leu Phe Leu Gly Ile
                20                  25                  30

Leu Lys Asn Trp Lys Glu Glu Ser Asp Arg Lys Ile Met Gln Ser Gln
            35                  40                  45

Ile Val Ser Phe Tyr Phe Lys Leu Phe Lys Asn Phe Lys Asp Asp Gln
 50                  55                  60

Ser Ile Gln Lys Ser Val Glu Thr Ile Lys Glu Asp Met Asn Val Lys
 65                  70                  75                  80

Phe Phe Asn Ser Asn Lys Lys Arg Asp Asp Phe Glu Lys Leu Thr
                 85                  90                  95

Asn Tyr Ser Val Thr Asp Leu Asn Val Gln Arg Lys Ala Ile His Glu
                100                 105                 110

Leu Ile Gln Val Met Ala Glu Leu Ser Pro Ala Ala Lys Thr Gly Lys
            115                 120                 125

Arg Lys Arg Ser Gln Met Leu Phe Gln Gly
        130                 135
```

<210> SEQ ID NO 12
<211> LENGTH: 166
<212> TYPE: PRT
<213> ORGANISM: Homo sapiens

<400> SEQUENCE: 12

```
Met Lys Tyr Thr Ser Tyr Ile Leu Ala Phe Gln Leu Cys Ile Val Leu
 1               5                  10                  15

Gly Ser Leu Gly Cys Tyr Cys Gln Asp Pro Tyr Val Gln Glu Ala Glu
                20                  25                  30

Asn Leu Lys Lys Tyr Phe Asn Ala Gly His Ser Asp Val Ala Asp Asn
            35                  40                  45

Gly Thr Leu Phe Leu Gly Ile Leu Lys Asn Trp Lys Glu Glu Ser Asp
 50                  55                  60

Arg Lys Ile Met Gln Ser Gln Ile Val Ser Phe Tyr Phe Lys Leu Phe
 65                  70                  75                  80

Lys Asn Phe Lys Asp Asp Gln Ser Ile Gln Lys Ser Val Glu Thr Ile
                 85                  90                  95

Lys Glu Asp Met Asn Val Lys Phe Phe Asn Ser Asn Lys Lys Lys Arg
```

```
            100                 105                 110

Asp Asp Phe Glu Lys Leu Thr Asn Tyr Ser Val Thr Asp Leu Asn Val
            115                 120                 125

Gln Arg Lys Ala Ile His Glu Leu Ile Gln Val Met Ala Glu Leu Ser
            130                 135                 140

Pro Ala Ala Lys Thr Gly Lys Arg Lys Arg Ser Gln Met Leu Phe Gln
145                 150                 155                 160

Gly Arg Arg Ala Ser Gln
                165

<210> SEQ ID NO 13
<211> LENGTH: 143
<212> TYPE: PRT
<213> ORGANISM: Homo sapiens

<400> SEQUENCE: 13

Gln Asp Pro Tyr Val Gln Glu Ala Glu Asn Leu Lys Lys Tyr Phe Asn
1               5                   10                  15

Ala Gly His Ser Asp Val Ala Asp Asn Gly Thr Leu Phe Leu Gly Ile
                20                  25                  30

Leu Lys Asn Trp Lys Glu Glu Ser Asp Arg Lys Ile Met Gln Ser Gln
            35                  40                  45

Ile Val Ser Phe Tyr Phe Lys Leu Phe Lys Asn Phe Lys Asp Asp Gln
        50                  55                  60

Ser Ile Gln Lys Ser Val Glu Thr Ile Lys Glu Asp Met Asn Val Lys
65                  70                  75                  80

Phe Phe Asn Ser Asn Lys Lys Lys Arg Asp Asp Phe Glu Lys Leu Thr
                85                  90                  95

Asn Tyr Ser Val Thr Asp Leu Asn Val Gln Arg Lys Ala Ile His Glu
            100                 105                 110

Leu Ile Gln Val Met Ala Glu Leu Ser Pro Ala Ala Lys Thr Gly Lys
        115                 120                 125

Arg Lys Arg Ser Gln Met Leu Phe Gln Gly Arg Arg Ala Ser Gln
    130                 135                 140

<210> SEQ ID NO 14
<211> LENGTH: 138
<212> TYPE: PRT
<213> ORGANISM: Homo sapiens

<400> SEQUENCE: 14

Gln Asp Pro Tyr Val Gln Glu Ala Glu Asn Leu Lys Lys Tyr Phe Asn
1               5                   10                  15

Ala Gly His Ser Asp Val Ala Asp Asn Gly Thr Leu Phe Leu Gly Ile
                20                  25                  30

Leu Lys Asn Trp Lys Glu Glu Ser Asp Arg Lys Ile Met Gln Ser Gln
            35                  40                  45

Ile Val Ser Phe Tyr Phe Lys Leu Phe Lys Asn Phe Lys Asp Asp Gln
        50                  55                  60

Ser Ile Gln Lys Ser Val Glu Thr Ile Lys Glu Asp Met Asn Val Lys
65                  70                  75                  80

Phe Phe Asn Ser Asn Lys Lys Lys Arg Asp Asp Phe Glu Lys Leu Thr
                85                  90                  95

Asn Tyr Ser Val Thr Asp Leu Asn Val Gln Arg Lys Ala Ile His Glu
            100                 105                 110

Leu Ile Gln Val Met Ala Glu Leu Ser Pro Ala Ala Lys Thr Gly Lys
```

```
              115                 120                 125
Arg Lys Arg Ser Gln Met Leu Phe Gln Gly
        130                 135

<210> SEQ ID NO 15
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 15
catacacgtt tgaggactat gatgtct                                      27

<210> SEQ ID NO 16
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 16
ttcggcgtct gcttgttgat c                                            21
```